United States Patent
Cho et al.

(10) Patent No.: US 10,869,600 B2
(45) Date of Patent: Dec. 22, 2020

(54) METHOD FOR NON-CONTACT ELECTROCARDIOGRAPHY MONITORING, CIRCUIT FOR NON-CONTACT ELECTROCARDIOGRAPHY MONITORING, AND APPARATUS FOR ELECTROCARDIOGRAPHY MONITORING USING THE SAME

(71) Applicant: KOREA ADVANCED INSTITUTE OF SCIENCE AND TECHNOLOGY, Daejeon (KR)

(72) Inventors: Seong Hwan Cho, Daejeon (KR); Jin Seok Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 223 days.

(21) Appl. No.: 15/578,598

(22) PCT Filed: Dec. 19, 2016

(86) PCT No.: PCT/KR2016/014879
§ 371 (c)(1),
(2) Date: Nov. 30, 2017

(87) PCT Pub. No.: WO2018/062630
PCT Pub. Date: Apr. 5, 2018

(65) Prior Publication Data
US 2018/0325375 A1    Nov. 15, 2018

(30) Foreign Application Priority Data
Sep. 29, 2016    (KR) ........................ 10-2016-0125253

(51) Int. Cl.
*A61B 5/00*    (2006.01)
*A61B 5/0402*    (2006.01)
(Continued)

(52) U.S. Cl.
CPC .......... *A61B 5/0006* (2013.01); *A61B 5/0245* (2013.01); *A61B 5/0402* (2013.01);
(Continued)

(58) Field of Classification Search
CPC combination set(s) only.
See application file for complete search history.

(56) References Cited

U.S. PATENT DOCUMENTS

2014/0200469 A1    6/2014    Bocko et al.

FOREIGN PATENT DOCUMENTS

KR    10-2006-0050892 A    5/2006
KR    10-2012-0102201 A    9/2012
(Continued)

OTHER PUBLICATIONS

YM Chi, C Maier, G Cauwenberghs, Ultra-High Input Impedance, Low Noise Integrated Amplifier for Noncontact Biopotential Sensing, Dec. 2011, IEEE Journal on emerging and selected topics in circuits and systems, vol. 1, No. 4, pp. 526-535. (Year: 2011).*

*Primary Examiner* — Michael W Kahelin
*Assistant Examiner* — Vynn V Huh
(74) *Attorney, Agent, or Firm* — Novick, Kim & Lee, PLLC; Sang Ho Lee

(57) ABSTRACT

A circuit for non-contact electrocardiography monitoring according to an embodiment of the present invention includes a non-contact monitoring unit for acquiring and outputting plus or minus monitoring signal of signal source with non-contact; an amplification control unit for amplifying the monitoring signal to output to output terminal; and an input impedance calibration circuit for being connected to input terminal and output terminal of the amplification control unit to process calibration of input impedance in calibration mode.

9 Claims, 7 Drawing Sheets

(51) Int. Cl.
    *A61B 5/0245*     (2006.01)
    *A61B 5/04*     (2006.01)

(52) U.S. Cl.
    CPC ........ *A61B 5/04017* (2013.01); *A61B 5/7214* (2013.01); *A61B 5/7225* (2013.01); *A61B 2562/0214* (2013.01)

(56) References Cited

FOREIGN PATENT DOCUMENTS

| | | |
|---|---|---|
| KR | 10-2016-0009982 A | 1/2016 |
| WO | 2015/131172 A1 | 9/2015 |
| WO | WO-2015131172 A1 * | 9/2015 |

* cited by examiner

METHOD FOR NON-CONTACT ELECTROCARDIOGRAPHY MONITORING, CIRCUIT FOR NON-CONTACT ELECTROCARDIOGRAPHY MONITORING, AND APPARATUS FOR ELECTROCARDIOGRAPHY MONITORING USING THE SAME

TECHNICAL FIELD

The present invention relates to a method, a circuit and an apparatus thereof for monitoring electric potential. More specifically, the present invention relates to a method for non-contact electrocardiography monitoring, a circuit for non-contact electrocardiography monitoring and an electrocardiography monitoring apparatus using the same.

BACKGROUND ART

In the field of measurement of bioelectricity signal, conventionally, conductive electrode is adhered directly to skin surface of human body for detection of signal. The bioelectricity signal may provide information needed in diagnosis of disease or prognosis of curing of human body. However, conductive electrode should be adhered directly to human body skin in the process of signal measurement. Owing to above, the examinee may have repulsion against test.

As a result, though real-time monitoring of long period should be performed in a state that the examinee is not conscious, it is difficult for wet electrode and dry electrode used conventionally to satisfy this condition. Therefore, methods to use electrical non-contact electrode (or non-contact electrode) appeared.

However, in non-contact way as above, to allow for monitoring electric potential of skin surface in a state that the examinee is wearing clothes, circuit configuration for increasing input impedance may be needed. However, a lot of conventional ways for settling the above are provided with positive feedback circuit for increasing input impedance, and are employing artificial control of resistance and capacitance thereof.

However, conventional ways for increasing impedance of non-contact electrocardiography monitoring like above have firstly limitation that it should use analog buffer of which gain of front stage amplifier of input terminal is 1. That is, buffer gain of first stage for configuration of the positive feedback is limited to equivalence input, by which there comes problem that not only noise efficiency of circuit is not good, but also needed power is increased. This may be cause difficulty in configuration of low-power system.

And, there comes another problem that, for positive feedback way of non-contact electrocardiography monitoring, direct and manual trimming about circuit configuration is needed. This is for prevention of system lability and oscillation according to increase of positive feedback value, which may cause problem that additional equipment, manpower and time becomes needed. As a result, this may cause problem that mass production of product is impossible and AS is difficult.

Accordingly, the above problems are not settled currently, and solution is wanted by which real-time monitoring of long period is possible and mass production is possible.

DISCLOSURE

Technical Problem

The present invention is to solve the problem like above, and object thereof is to provide a method for non-contact electrocardiography monitoring, a circuit for non-contact electrocardiography monitoring and an apparatus for electrocardiography monitoring using the same, by which real-time monitoring of long period is possible and mass production is possible, by enabling amplification based on high input impedance with configuration of low-power and low-noise circuit.

Technical Solution

The circuit according to an embodiment of the present invention to solve problems above is a circuit for non-contact electrocardiography monitoring, including a non-contact monitoring unit acquiring and outputting plus or minus monitoring signal of signal source with non-contact; an amplification control unit for amplifying the monitoring signal to output to output terminal; and an input impedance calibration circuit for being connected to input terminal and output terminal of the amplification control unit to process calibration of input impedance in calibration mode.

The method according to an embodiment of the present invention to solve problems above is a method for non-contact electrocardiography monitoring including steps of processing calibration on input impedance of amplification control unit in foreground calibration mode; entering monitoring mode when the calibration being finished; acquiring plus or minus monitoring signal of signal source with non-contact in monitoring mode; and amplifying and outputting the monitoring signal.

On the other hand, the apparatus according to an embodiment of the present invention to solve problems above may be implemented as an apparatus for electrocardiography monitoring including the circuit.

Advantageous Effects

According to an embodiment of the present invention, by using shield circuit of input terminal, gain limit of input terminal buffer becomes free, by which super low-power, low-noise system of 1 micro watt or less may be realized.

And, according to an embodiment of the present invention, via foreground calibration performed automatically before electrocardiography monitoring, high impedance amplification can be driven stably. Accordingly, inconvenience of artificial trimming can be removed, and additional equipment or manpower and time cost for stability can be excluded, by which there comes great effect that possibility of mass production increases.

DETAILED DESCRIPTION OF THE PREFERRED EMBODIMENT

Figure 1:
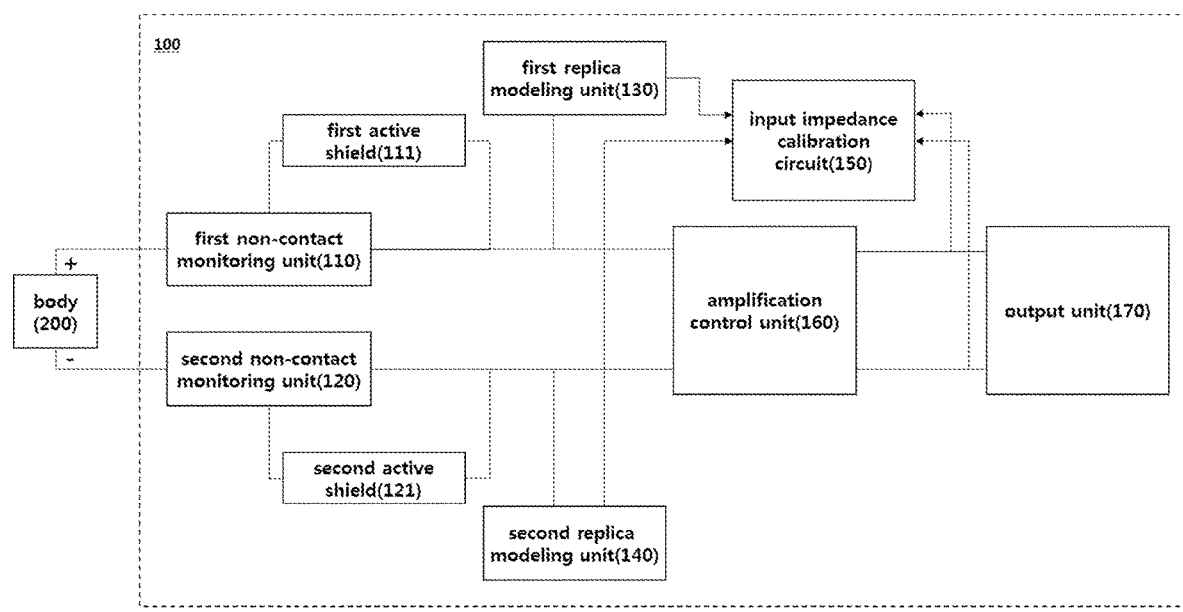
FIG. 1 shows a block diagram showing conceptually the overall system according to an embodiment of the present invention.

Description hereinafter is only for illustration of principle of the present invention. Therefore, though not described or illustrated clearly in the specification, an ordinary person in the art may realize principle of the present disclosure and make invention of a variety of apparatus included in concept and scope of the present invention. And, all the conditional terms and embodiments written in the present specification is, as a principle, intended clearly for object for understanding concept of the present invention, and should be understood as not be restrictive by specifically illustrated embodiments and states.

And, not only principle, view point and embodiments of the present invention, but also all the detailed description over specific embodiment should be understood as to intend to include any structural and functional equivalence of these items. And these equivalences should be understood as to include not only equivalence of currently publicly known, but also equivalence to be developed in the future, that is all the elements invented to perform the same function regardless of structure.

Therefore, for example, block diagram of the present specification should be understood as to show conceptual point of view of illustrative circuit which actualize principle of the present invention. Similarly, all the flow chart, state transition diagram, pseudo code, or the like may be shown practically in a computer readable medium, and should be understood as to show a variety of process performed by computer or processor, regardless of whether computer or processor is depicted explicitly.

Function of processor, or a variety of elements depicted on drawings including function block shown in similar concept thereto may be provided by using not only exclusive hardware but also hardware having faculty to implement software in relation to proper software. When provided by processor, the function may be provided by single exclusive process, single shared processor or a plurality of individual processors, a portion of which may be shared.

And, explicit use of terms of processor, control or terms presented in similar concept thereto should not be interpreted citing exclusively hardware having faculty of implementing software, but should be understood as to include implicitly digital signal processor (DSP) hardware, ROM, RAM and non-volatile memory for storing software without limitation. And well-known or commonly used other hardware may be included.

In claims of the specification, element expressed as means to preform function written in detailed description is intended to include, for example, combination of circuit elements performing the function, or all the method performing function including software of every type including firmware/micro code or the like, which is combined to proper circuit for implementing the software to perform the function. Since the present invention defined by claims like above is combined to functions provided by means enumerated in variety and is combined to way required by claims, any means capable of providing the function should be understood as equivalent to the one captured from the present specification.

Objects, features and advantages above may be clarified more through following detailed description relating attached drawings, by which an ordinary person in the art of technical field in which the present invention pertains may implement technical idea of the present invention with ease. And, specific description on publicly known technology related to the present invention may be omitted in case that detailed description is determined to blur the gist of the present invention.

FIG. 1 shows a block diagram showing conceptually overall system according to an embodiment of the present invention.

Referring to FIG. 1, non-contact electrocardiography system according to an embodiment of the present invention may be configured with a body 200 which is signal source and electrocardiography monitoring apparatus 100 connected indirectly with non-contact, and the electrocardiography monitoring apparatus 100 may configured to include first non-contact monitoring unit 110, second non-contact monitoring unit 120, first active shield 111, second active shield 121, first replica modeling unit 130, second replica modeling unit 140, input impedance calibration circuit 150, amplification control unit 160 and output unit 170.

At the first non-contact monitoring unit 110 and second non-contact monitoring unit 120, each of condenser and front stage amplifier may be provided disposed between human body and electrocardiography monitoring apparatus 100 and formed between human body and non-contact type electrode, by which first input electrocardiography signal and second input electrocardiography signal (ECG, electrocardiogram) by plus electrode and minus electrode according to frequency change of bio signal may be acquired respectively, and be delivered to the amplification control unit 160.

And, according to an embodiment of the present invention, the first active shield 111 and second active shield 121 corresponding to each of the non-contact monitoring unit 110 and 120 may be provided. Each of active shield 111 and 121 may include shield circuit and active analog buffer for removing parasitic capacitance for input electrocardiography signal voltage and for enabling low-power, low-noise driving. More details of above will be described using FIG. 3.

And, each of replica modeling unit 130 and 140 generates replica node voltage for capacitance calibration and provide it to the input impedance calibration circuit 150. Since parasitic capacitance and source impedance of input signal are coexisting on signal line, this is to exclude the above in compensation of parasitic capacitance parasitic on signal line, and the input impedance calibration circuit 150 can perform calibration process using signal inputted from the replica node.

That is, in case that original signal line is inputted to calibration circuit directly, incorrect compensation may be realized. Therefore, the replica modeling units 130 and 140 operates in calibration mode of the electrocardiography monitoring apparatus 100 to output input signal to the input impedance calibration circuit 150.

On the other hand, the input impedance calibration circuit 150 may include circuit for minimizing parasitic capacitance of input terminal by performing foreground calibration before electrocardiography monitoring according to an embodiment of the present invention.

For the above, the input impedance calibration circuit 150 may include one or more switch circuits connected to the replica modeling units 130 and 140, and calibration signal generation unit, calibration logic processing unit and positive feedback capacitor array unit which may be described later.

Accordingly, the input impedance calibration circuit 150 may perform logic process on positive feedback capacitor array according to output of replica modeling units 130 and 140 operating in calibration mode and calibration signal, to minimize parasitic capacitance into reference value. For the above, in calibration mode, reset phase and calibration phase may be repeatedly controlled, and each of reset switches for the above may be included.

On the other hand, the amplification control unit 160 may include core amplifier for amplifying input signal according to each of operation mode and for outputting to the output unit 170.

Firstly, the amplification control unit 160 may amplify via core amplifier according to output of replica modeling units 130 and 140 in calibration mode, and output amplified output signal to the input impedance calibration circuit 150. Here, input impedance calibration circuit 150 can be controlled at optimized state for electrocardiography monitoring, and input terminal of the non-contact monitoring units 110 and 120 may be controlled at off state.

And then, the amplification control unit 160 may be inputted with signal of which capacitance is reduced and impedance is increased from signal inputted from each of non-contact monitoring units 110 and 120 by being processed by active shields 111 and 121 of input terminal, from which amplified electrocardiography signal may be outputted. At this moment, circuit at the side of replica modeling units 130 and 140 can be controlled in off state.

The output unit 170 may include one or more output modules for outputting electrocardiography monitoring result from amplified signal. The output module may be, for example, a configuration of terminal apparatus capable of process, output and display and the like of bio information, and output module of a variety of computer apparatus such as personal computer, smart phone, tablet PC etc. may be illustrated.

Hereinafter, more detailed embodiments will be described through circuit configuration with reference to FIG. 2 to FIG. 11.

Figure 2:
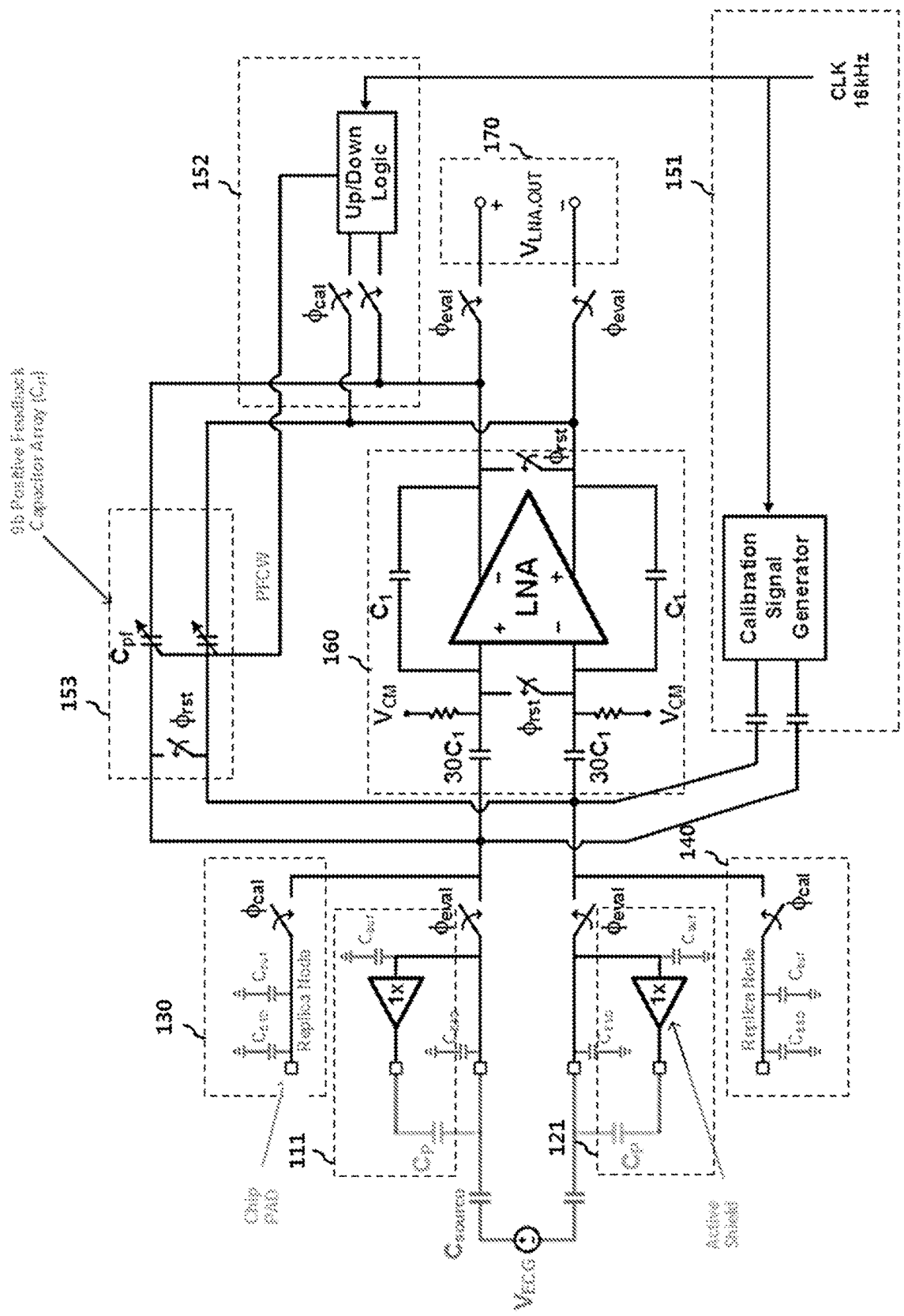
FIG. 2 shows a circuit diagram for specific explanation of case in which a system according to an embodiment of the present invention is realized as a circuit.

FIG. 2 shows a circuit diagram for more detailed explanation of case that system according to an embodiment of the present invention is realized as circuit.

Referring to FIG. 2, the electrocardiography monitoring apparatus 100 according to an embodiment of the present invention may be configured to include first non-contact monitoring unit 110, second non-contact monitoring unit 120, first active shield 111, second active shield 121, first replica modeling unit 130, second replica modeling unit 140, input impedance calibration circuit 150, amplification control unit 160 and output unit 170 realized as circuit elements.

As described above, each of non-contact monitoring units 110 and 120 may be configured to include each of active shield circuits 111 and 121, and each of active shield circuits 111 and, 121 may include active amplifier for design of low-power buffer.

Figure 3:
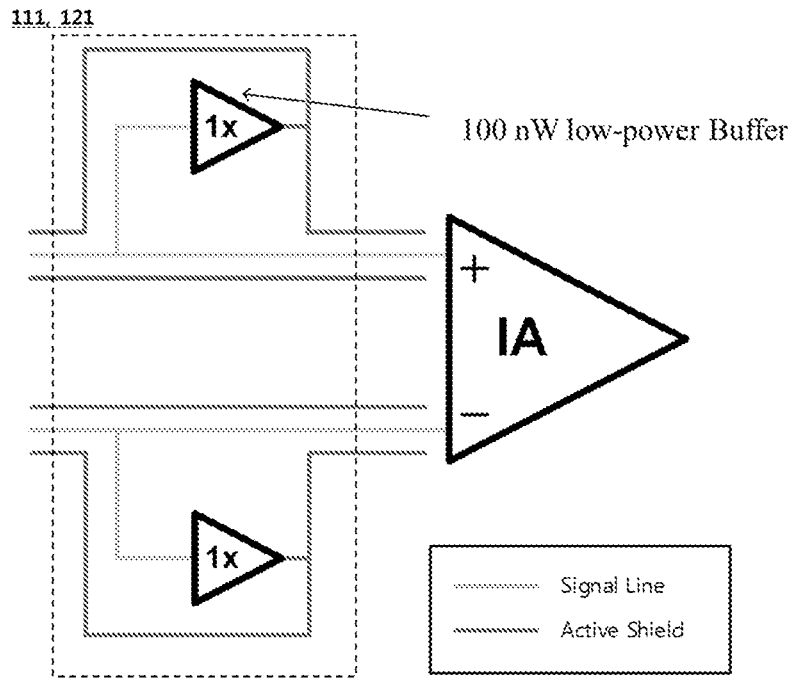
FIG. 3 shows a diagram for explanation of shield circuit according to an embodiment of the present invention.

Here, referring to FIG. 3, frequency regions of first and second ECG signal inputted to each of non-contact monitoring units 110 and 120 is 0.5 to 50 Hz, and input signal may be delivered to active shields 111 and 121 and be processed.

And, parasitic capacitance between input terminal of non-contact monitoring units 110 and 120 and active shield circuit may be level of about 20 to 200 pF. Here, type of needed active shield may be analog buffer of which gain is 1.

Therefore, active shield circuits 111 and 121 according to an embodiment of the present invention may be configured so that input terminal of low-power analog buffer amplifier of which output terminal is connected to one side of shield is connected in parallel between input terminal of non-contact monitoring units 110 and 120 and input terminal of core amplifier of the amplification control unit 160. Accordingly, voltage of input signal may be filtered by active analog buffer and shield circuit, by which power consumption can be reduced to about 100 nW level without front stage amplifier of which gain is 1, and low-noise process can be performed.

That is, as shown in FIG. 3, active shield circuits 111 and 121 can be configured that input terminal of active analog buffer of which output terminal is connected to shield enclosing signal line is connected to signal line, by which low-power low-noise shield circuit can be realized.

On the other hand, as described above, each of replica modeling units 130 and 140 may be provided with one or more switch and capacitance for generating replica node input signal for operation of the input impedance calibration circuit 150

As described above, the replica modeling units 130 and 140 are to exclude source impedance of original signal line in calibration for compensation of capacitance parasitic on signal line, and can be operative in calibration mode. For the above, in each of replica modeling units 130 and 140, replica node may be provided, and switch Φcal connected to node may be turned on in calibration mode. On the other hand, in monitoring mode, switch Φcal may be turned off, while Φeval, on.

And, as shown in FIG. 2, on replica node, replica capacitance having the same size as that of capacitance CESD and capacitance Cbuf existing on signal line may be provided, by which accurate calibration in a state that source impedance is excluded may be enabled.

On the other hand, the input impedance calibration circuit 150 may be connected to the replica modeling units 130 and 140 and core amplifier output of the amplification control unit 160, to configure loop for minimize parasitic capacitance of input terminal, and may include calibration signal generation unit 151, calibration logic processing unit 152 and positive feedback capacitor array unit 153.

Firstly, in calibration mode, connection of the input impedance calibration circuit 150 to original signal line is turned off by switch operation as described above, and may be connected to each of replica node of replica modeling units 130 and 140.

And, in calibration mode, the calibration signal generation unit 151 may generate small signal clock for calibration and apply to calibration signal generator and logic processing unit 152.

Figure 4:
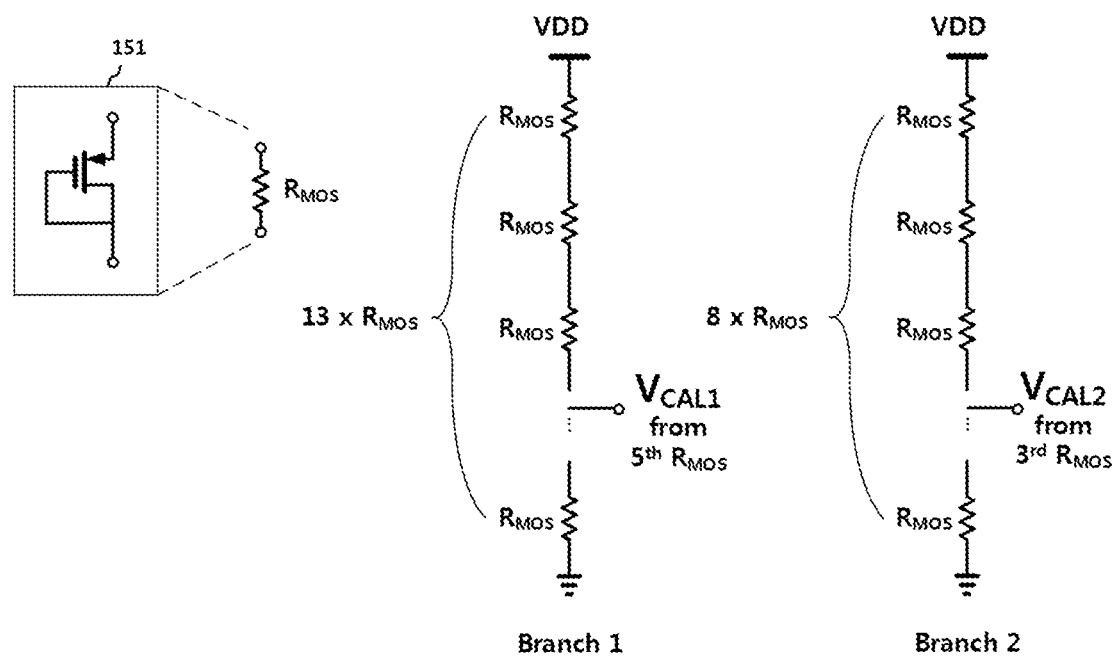
FIG. 4 and FIG. 5 show diagrams for explanation of calibration signal generation circuit according to an embodiment of the present invention.
Figure 5:
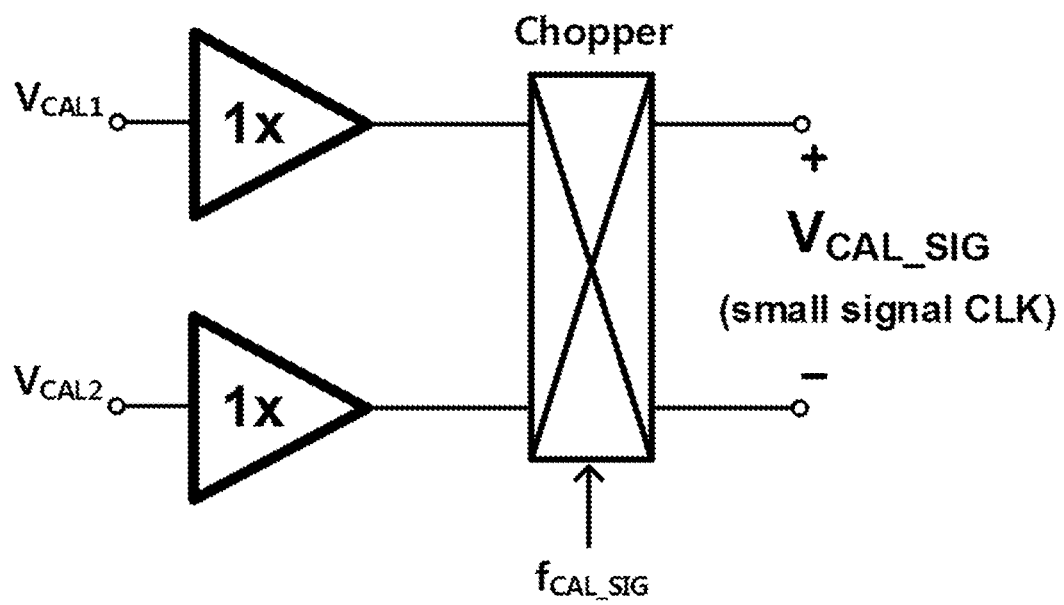

In small signal clock, FIG. 4 and FIG. 5 may be referred. FIG. 4 and FIG. 5 are diagrams for explanation of calibration signal generation circuit according to an embodiment of the present invention.

According to an embodiment of the present invention, calibration signal generation circuit may be configured with circuit based on PMOS diode stack. That is, by stacking in a state that PMOS diode are connected, voltage divider that can be driven with low-power can be realized. According to such way, calibration signal generation unit 151 according to an embodiment of the present invention may include two PMOS diode-stacked branches, and can generate small signal clock for calibration using difference thereof between two branches.

For example, as shown in FIG. 4, the calibration signal generation unit 151 may be configured to connect serially thirteen resistances R_MOS on branch 1 to extract voltage VCAL1 at fifth resistance, while may be configured selectively to connect serially eight resistances R_MOS on branch 2 to extract voltage VCAL2 at third resistance.

At this time, difference value of VCAL1 and VCAL2 may be represented as following:

$$V_{CAL1} - V_{CAL2} = \left(\frac{5}{13} - \frac{3}{8}\right) VDD = \frac{1}{104} VDD \approx 0.01 \cdot VDD \quad \text{[Equation 1]}$$

According to above, generated voltage on two branches may be controlled on and off by chopper as shown in FIG. 5, to be outputted as small signal clock signal (VCAL_SIG) for calibration.

On the other hand, referring to FIG. 2 back, the logic processing unit 152 can perform calibration process by repetitively adjusting variable capacitance C_pf of the positive feedback capacitor array unit 153 according to predetermined logic in case that signal for the calibration is applied.

For the above, the logic processing unit 152 may include one or more logic element for performing logic process as following:

Firstly, the logic processing unit 152 can sample output voltage from output terminal of LNA (Low-Noise Amplifier) which is core amplifier of the amplification control unit 160.

And, the logic processing unit 152 can determine whether size of sampled output voltage signal is larger than preset logic threshold value (Logic Threshold, Vth) or not.

And, the logic processing unit 152 may generate Down signal in case that sampled voltage is larger than Vth, while Up signal, in case that sampled voltage is smaller.

Accordingly, by increasing PFCW (Positive Feedback Control Word) by 1 when Up signal is generated, while decreasing, when Down signal, the logic processing unit 152 can adjust capacitance of variable capacitance of the positive feedback capacitor array unit 153.

And, the logic processing unit 152 can initialize signal input by controlling reset switch Φ_rst, and can perform the process procedures again. And, the process can be performed repeatedly in sequence till predetermined halt condition is satisfied.

After that, in case that halt condition is satisfied, the logic processing unit 152 may deliver mode switching request to the amplification control unit 160, and the amplification control unit 160 may control each switch in case that halt condition is satisfied, to turn off connection between input impedance calibration circuit 150 and replica modeling units 130 and 140, and to connect to signal line, by which have it to operate in monitoring mode in which input signal can be monitored.

Figure 6:
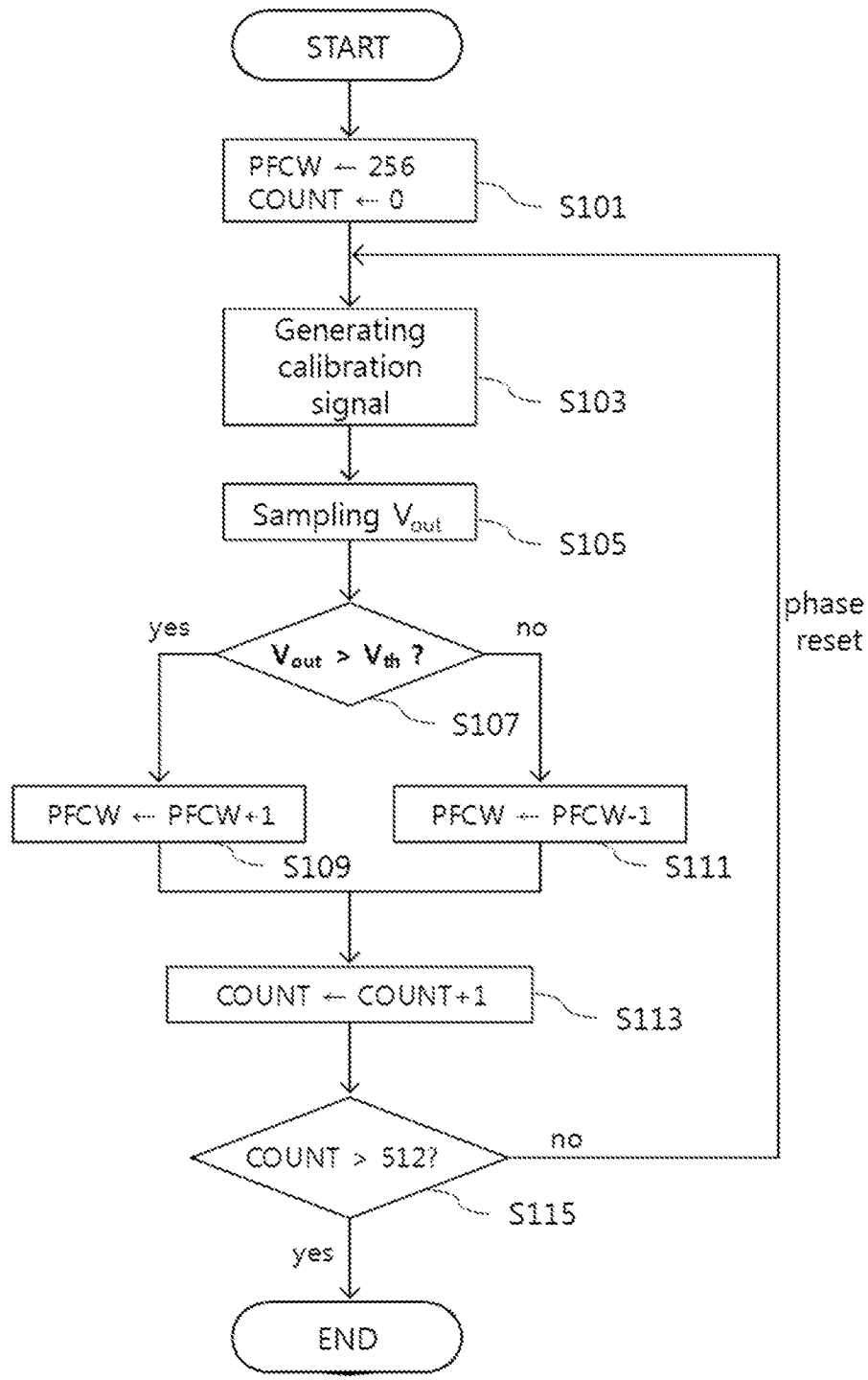
FIG. 6 shows a flow chart for explanation of calibration method for non-contact electrocardiography monitoring according to an embodiment of the present invention.

For operation of the logic processing unit 152 like above, FIG. 6 discloses a flow chart for explanation of calibration method for non-contact electrocardiography monitoring according to an embodiment of the present invention.

FIG. 6 illustrates a case that initial PFCW value is 256 and halt COUNT value is 512, and firstly, the logic processing unit 152 may output signal for setting COUNT to 0 and PFCW value to 256 to the positive feedback capacitor array unit 153 (S101).

And, when calibration signal is generated from the calibration signal generation unit 151 (S103), the logic processing unit 152 may sample V_out from output of core amplifier of the amplification control unit 160 according to calibration signal (S105).

After that, the logic processing unit 152 may judge whether V_out is larger than preset threshold value V_th or not (S107).

Here, in case of larger than threshold value, the logic processing unit 152 can increase PFCW value by 1 (S109), while in case of smaller, can decrease (S111).

After that, the logic processing unit 152 may increase COUNT value by 1 (S113), and judge whether increased value is larger than predetermined halt condition 512 or not (S115).

Here, in case COUNT is larger than halt condition, finish phase of the logic processing unit 152 may be proceeded, and may be switched to monitoring mode.

On the other hand, COUNT is smaller than halt condition, phase reset according to reset signal is processed, and steps of S103 to S115 based on increased COUNT respectively may be performed repetitively till halt condition is satisfied.

Figure 7:
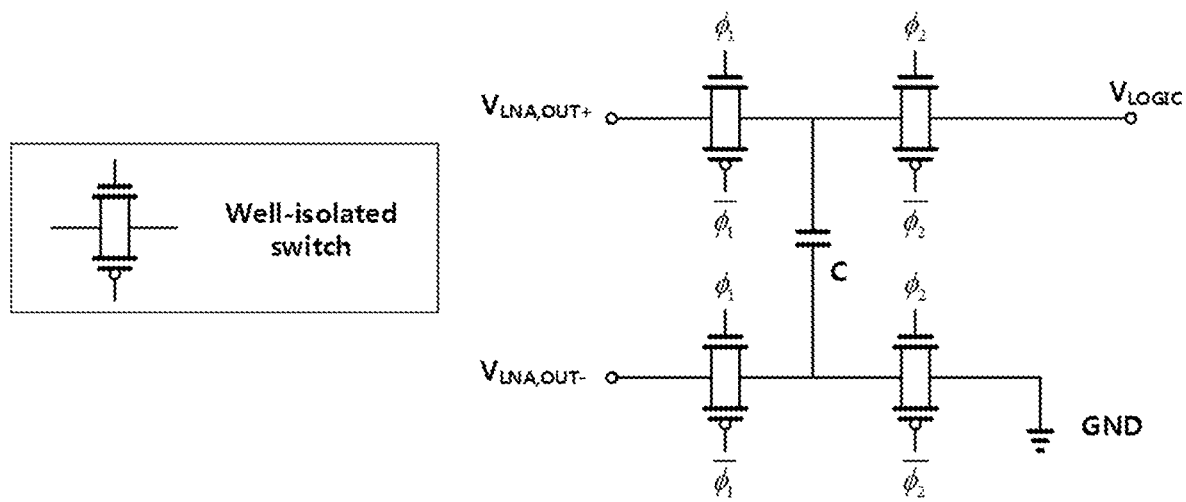
FIG. 7 and FIG. 8 show diagrams for explanation of calibration logic circuit according to an embodiment of the present invention.
Figure 8:
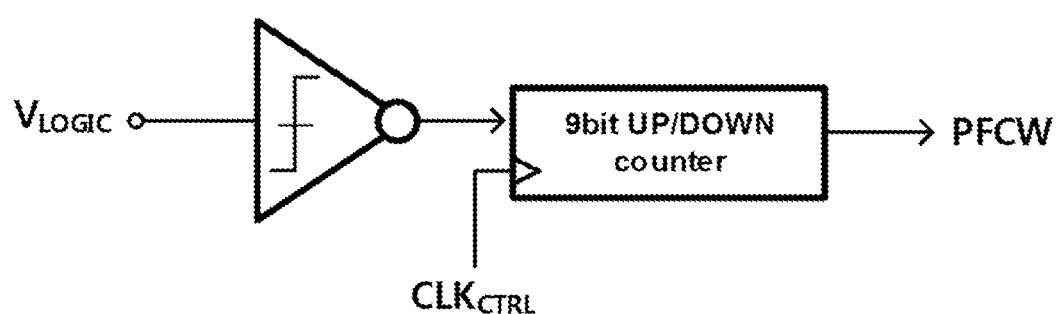

Here, FIG. 7 and FIG. 8 are drawings for more specific explanation of variable capacitance control of calibration logic circuit according to an embodiment of the present invention, and the logic processing unit 152 may be divided largely into differential phase sampler (Differential Charge Sampler) and threshold logic control circuit (Logic Threshold and Control Circuit).

The differential phase sampler may be configured as shown in FIG. 7, and may receive differential output of core amplifier LNA as input signal. And, differential phase sampler may include a plurality of insulating switches for processing level shift with reference to GND according to input signal to store to capacitance.

On the other hand, the threshold logic control circuit (Logic Threshold and Control Circuit) may be configured as shown in FIG. 8. The threshold logic control circuit may receive V_LOGIC which is output of the differential phase sampler as input. And, threshold logic control circuit may determine Up/Down signal with reference to inverter logic threshold value set according to threshold value like above, to control 9 bits counter for PFCW output, and according to the counter output, variable capacitance C_pf of the positive feedback capacitor array unit 153 may be controlled.

On the other hand, referring to FIG. 2 back, overall system of electrocardiography monitoring apparatus 100 may be switched to monitoring mode back after the calibration mode is finished. According to monitoring mode switching, calibration mode switches Φ_cal may be switched off, while monitoring mode switches Φ_eval may be switched on, by which input signal monitored from body may be amplified to be outputted respectively to input terminal of the output unit 170.

According to structure as above, the electrocardiography monitoring apparatus 100 can process calibration for input impedance of amplification control unit in foreground calibration mode before monitoring, and when the calibration is finished, monitoring mode is entered, and in monitoring mode, plus or minus monitoring signal of signal source may be acquired with non-contact, and the monitoring signal can be amplified and outputted.

And, according to an embodiment of the present invention like above, in the electrocardiography monitoring apparatus

100 capable of non-contact monitoring, super low-power low-noise amplifier consuming power of 1 uW or less can be designed, through which health care system capable of real-time monitoring of long period can be built up. Especially, through foreground calibration, without process of artificial tuning or trimming, minimization of parasitic impedance and optimization of system impedance for optimal electrocardiography monitoring may be enabled at chip alone, by which possibility of mass production can be increased.

Figure 9:
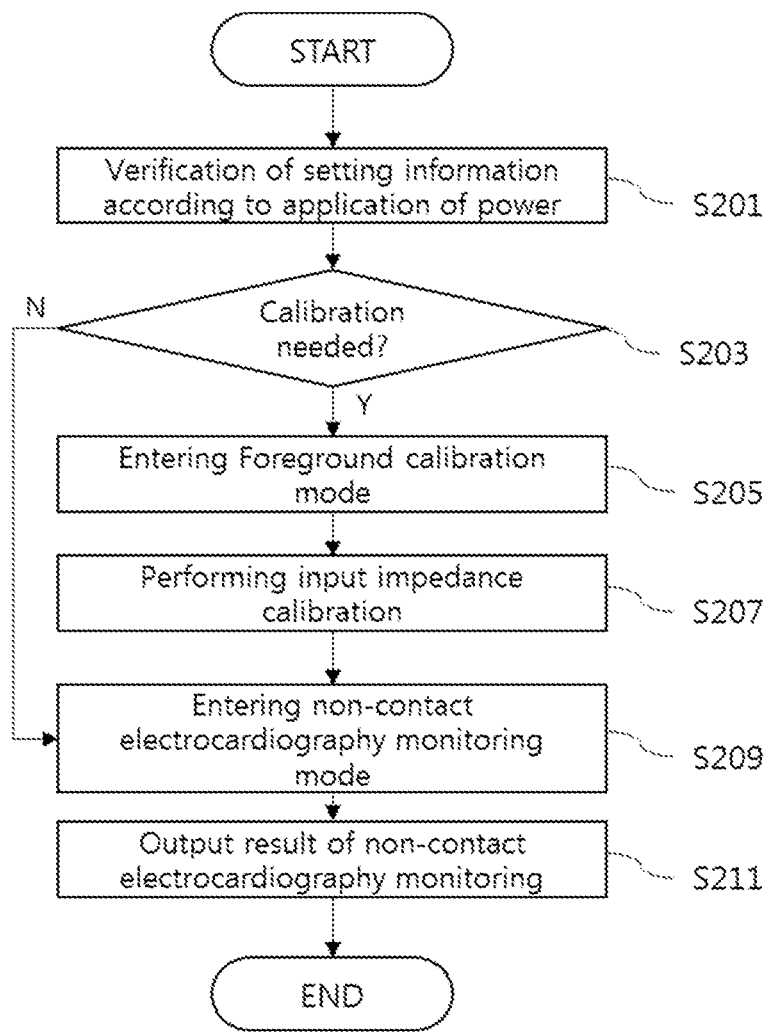
FIG. 9 shows a flow chart for explanation of monitoring method using apparatus for electrocardiography monitoring including calibration circuit according to an embodiment of the present invention.

FIG. 9 shows a flow chart for explanation of monitoring method using electrocardiography monitoring apparatus including calibration circuit according to an embodiment of the present invention.

According to an embodiment of the present invention, electrocardiography monitoring apparatus 100 according to an embodiment of the present invention may include mode entering processor for preprocessing calibration method like above automatically for user's convenience.

Accordingly, referring to FIG. 9, electrocardiography monitoring apparatus 100 according to an embodiment of the present invention may verify setting information on calibration mode according to application of power (S201).

And, the electrocardiography monitoring apparatus 100 may judge whether calibration is needed or not (S203).

For the above, the electrocardiography monitoring apparatus 100 may further include memory in which predetermined setting information is stored, and in the memory, setting information corresponding to entering condition and timing for foreground calibration mode may be included.

Accordingly, the electrocardiography monitoring apparatus 100 may verify condition information and timing set by user or manufacturer, and can determine whether calibration is needed or not at current timing. For example, in case that repeated monitoring is performed to the same user wearing the same clothes, direct monitoring without calibration can be performed according to user setting. On the other hand, in case that user is changed or after predetermined period is passed, automatic entrance to calibration mode may be set.

In case that calibration is needed, the electrocardiography monitoring apparatus 100 may enter foreground calibration mode (S205), to perform foreground calibration for input impedance including above steps of S101 to S115 (S207).

On the other hand, in case that calibration is completed or unnecessary, the electrocardiography monitoring apparatus 100 may enter non-contact electrocardiography monitoring mode (S209).

According to entrance to monitoring mode, the electrocardiography monitoring apparatus 100 may output electrocardiography monitoring signal amplified by amplification control unit 160 through output unit 170 based on monitoring signal inputted from non-contact monitoring units 110 and 120 (S211). Form of output may have a variety of types like display, sound, vibration or the like.

On the other hand, method according to a variety of embodiments of the present invention above may be realized as program code, and be provided to each server or instruments in a state stored in variety of non-transitory readable medium (non-transitory computer readable medium).

The non-transitory readable medium means medium capable of storing data semi permanently, and being read by instruments, not medium storing data during a short instance like register, cache, memory or the like. Specifically, above various applications or programs may be stored in non-transitory readable medium such as CD, DVD, hard disk, blue-ray disk, USB, memory card, ROM or the like and be provided.

And, though desirable embodiments of the present invention have been depicted and described above, the present invention is not limited to such specific embodiments, but without escaping from gist of the present invention claimed in claims, a variety of modified implementation may be of course possible by an ordinary skilled person in the art, and these modified implement should not be understood to separately from technical idea or perspective of the present invention.

What is claimed is:

1. A circuit for non-contact electrocardiography monitoring comprising:
   a non-contact monitoring circuit unit acquiring and outputting a monitoring signal of a signal source with non-contact;
   an amplification control circuit amplifying the monitoring signal to output to an output terminal; and
   an input impedance calibration circuit connected to an input terminal of the amplification control circuit and the output terminal of the amplification control circuit and processing a calibration of an input impedance in a calibration mode,
   wherein the input impedance calibration circuit comprises:
   a calibration signal generator generating a clock signal for a calibration in the calibration mode;
   a logic processing circuit performing logic process according to the clock signal with an input and output of the amplification control circuit; and
   a positive feedback capacitor array unit variably controlled according to control of the logic processing circuit,
   wherein the calibration signal generator comprises a voltage divider outputting differential signal of a first branch circuit and a second branch circuit, each of the first and second branch circuits including a PMOS diode stack comprising a plurality of resistances,
   wherein the first branch circuit includes a first number of serially connected resistances and the second branch circuit includes a second number of resistances wherein the first number and the second number are different from each other,
   wherein the voltage divider extracts a first voltage VCAL1 from a specific resistance of the first branch circuit, extracts a second voltage VCAL2 from a specific resistance of the second branch circuit, and controls on and off of a chopper with the VCAL1 and VCAL2 to output a small signal clock signal for the calibration of the logic processing circuit which is repetitively adjusting variable capacitance of the positive feedback capacitor array unit by using the small signal clock signal.

2. The circuit for non-contact electrocardiography monitoring according to claim 1, further comprising:
   one or more replica modeling circuits connecting an output terminal of a replica node connected to capacitances having the same capacitance as that of a signal line to the input terminal of the amplification control circuit and the input impedance calibration circuit in the calibration mode,
   wherein the one or more replica modeling circuits generates a replica node voltage for capacitance calibration and provides the replica node voltage to the input impedance calibration circuit to exclude source impedance of an original signal line in calibration for compensation of capacitance parasitic on the signal line.

3. The circuit for non-contact electrocardiography monitoring according to claim 2, wherein, the input terminal of the amplification control circuit inputted from the non-contact monitoring circuit is controlled in an off state.

4. The circuit for non-contact electrocardiography monitoring according to claim 1, wherein the logic processing circuit performs the logic process by repetitively adjusting variable capacitance of the positive feedback capacitor array unit, according to a comparison logic between a sampling value of output of the amplification control circuit and a predetermined threshold value in the calibration mode.

5. The circuit for non-contact electrocardiography monitoring according to claim 1, wherein the logic processing circuit comprises:
   a differential phase sampler receiving a differential output of a core amplifier as an input signal, and processing a level shift with reference to a GND, and storing a sampled signal to a capacitance, to sample output signals of the amplification control circuit.

6. The circuit for non-contact electrocardiography monitoring according to claim 5, wherein the logic processing unit comprising circuit further comprises:
   a threshold logic control circuit for receiving an output of the differential phase sampler, and determining an Up or Down signal with reference to a preset inverter logic threshold value, to control a counter connected to the positive feedback capacitor array unit.

7. The circuit for non-contact electrocardiography monitoring according to claim 1, wherein the non-contact monitoring circuit comprises an active shield circuit,
   wherein the active shield circuit includes an analog buffer amplifier in which an output terminal is connected to one side of a shield enclosing an input signal line, and wherein an input terminal of the analog buffer amplifier is connected in parallel between an input terminal of the non-contact monitoring circuit and an input terminal of a core amplifier of the amplification control circuit.

8. The circuit for non-contact electrocardiography monitoring according to claim 1, wherein the monitoring signal include a plus or minus voltage signal acquired from the signal source with non-contact.

9. A computer apparatus for non-contact electrocardiography monitoring comprising:
a circuit for non-contact electrocardiography monitoring;
wherein the circuit comprises:
a non-contact monitoring circuit acquiring and outputting a monitoring signal of a signal source with non-contact;
an amplification control circuit amplifying the monitoring signal to output to an output terminal; and
an input impedance calibration circuit connected to an input terminal of the amplification control circuit and the output terminal of the amplification control circuit and processing a calibration of an input impedance in a calibration mode,
wherein the input impedance calibration circuit comprises:
a calibration signal generator generating a clock signal for calibration in the calibration mode;
a logic processing circuit performing logic process according to the clock signal with an input and output of the amplification control circuit; and
a positive feedback capacitor array unit variably controlled according to control of the logic processing circuit,
wherein the calibration signal generator comprises a voltage divider outputting differential signal of a first branch circuit and a second branch circuit, each of the first and second branch circuits including a PMOS diode stack comprising a plurality of resistances,
wherein the first branch circuit includes a first number of serially connected resistances, and the second branch circuit includes a second number of resistances wherein the first number and the second number are different from each other,
wherein the voltage divider extracts a first voltage VCAL1 from a specific resistance of the first branch circuit, extracts a second voltage VCAL2 from a specific resistance of the second branch circuit, and controls on and off of a chopper with the VCAL1 and VCAL2 to output a small signal clock signal for the calibration of the logic processing circuit which is repetitively adjusting variable capacitance of the positive feedback capacitor array unit by using the small signal clock signal.

* * * * *